United States Patent [19]
Sturm

[11] Patent Number: 5,457,539
[45] Date of Patent: Oct. 10, 1995

[54] ON-LINE COMPENSATION FOR DEFLECTION IN INSTRUMENTS USING FOCUSED BEAMS

[75] Inventor: Steven P. Sturm, Columbus, Ohio

[73] Assignee: ABB Industrial Systems, Inc., Columbus, Ohio

[21] Appl. No.: 79,344

[22] Filed: Jun. 18, 1993

[51] Int. Cl.$^6$ .......................... G01N 21/84; G01N 21/00
[52] U.S. Cl. .......................... 356/429; 356/73; 356/431; 356/435; 250/559.01
[58] Field of Search .................................. 356/429, 430, 356/73, 431, 435; 250/559, 571

[56] References Cited

U.S. PATENT DOCUMENTS

| | | | |
|---|---|---|---|
| 4,678,915 | 7/1987 | Dahlquist et al. | 250/358.1 |
| 5,004,928 | 4/1991 | Suzuki et al. | 356/429 |
| 5,054,930 | 10/1991 | Adelson | 356/429 |
| 5,117,686 | 6/1992 | Lorenz | 73/159 |
| 5,233,195 | 8/1993 | Hellstrom et al. | 250/360.1 |
| 5,237,181 | 8/1993 | Kerkhoff et al. | 356/429 |

*Primary Examiner*—Rolf Hille
*Assistant Examiner*—David Ostrowski
*Attorney, Agent, or Firm*—Killworth, Gottman, Hagan & Schaeff

[57] ABSTRACT

A focused light beam instrument measures characteristics of webs of sheet material. The instrument and a reference surface, a backing tile in a carousel, are on opposite sides of the web which is maintained a fixed distance from the reference surface by a Bernoulli hold down device such that variations in the gap affect the beam focus. The instrument and reference surface scan the web via a scanning frame. The instrument is calibrated-standardized in an off sheet position where a first surface, a carousel backing tile, is moved opposite to the instrument and in the plane of the web. The instrument measures the first surface and a second surface, another carousel backing tile, which is moved opposite to the instrument but spaced farther from or closer thereto than the first surface. The distance of the instrument from the web is calculated from the difference between the measurements of the first and second surfaces. The calculated distance is used to determine an operating position on an instrument response curve and the instrument is calibrated accordingly. A second or third order polynomial is fitted to the instrument response curve and differentiated at the operating point on the curve to determine the rate of change of the measurement characteristic of the instrument at that point. Gap changes and the determined rate of change of the measurement characteristics are used to compensate gap change errors in measurements made by the instrument.

20 Claims, 3 Drawing Sheets

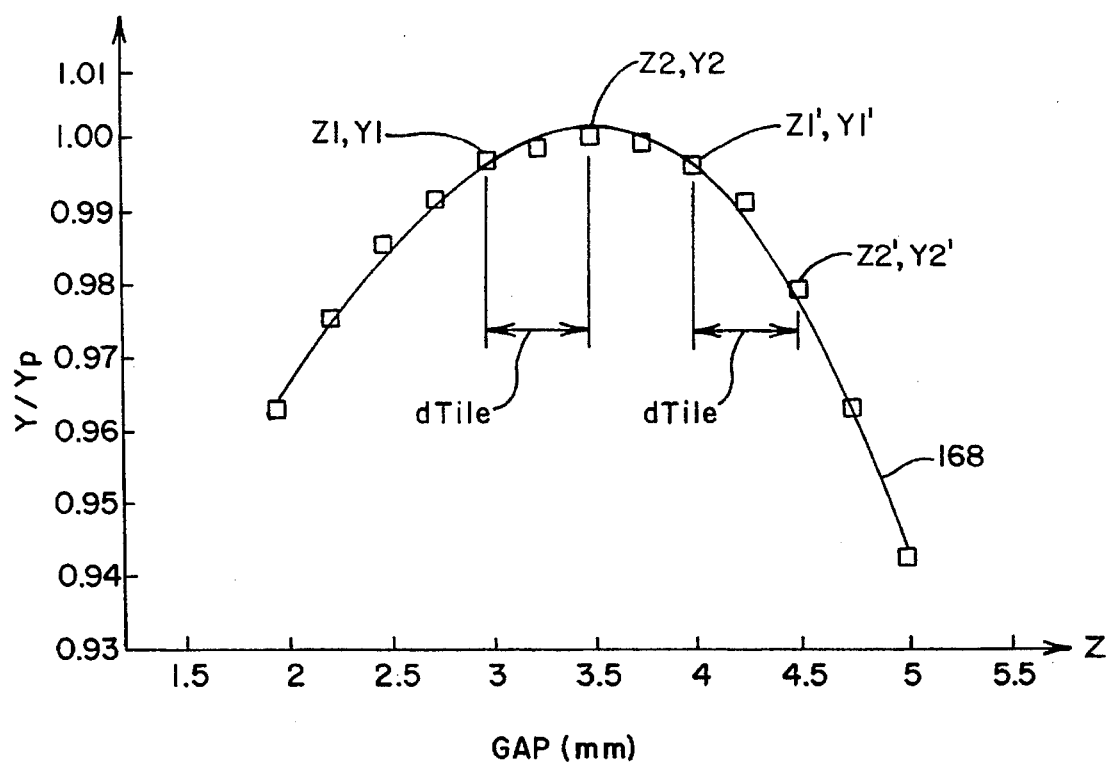

ON-LINE COMPENSATION FOR DEFLECTION IN INSTRUMENTS USING FOCUSED BEAMS

BACKGROUND OF THE INVENTION

The present invention relates in general to the measurement of various parameters or characteristics of a web of sheet material as it is being manufactured and, more particularly, to a method and apparatus for compensating for deflections within instruments measuring web characteristics by means of a focused radiation beam, such as a focused beam of light.

Many on-line instruments use focused radiation beams to measure characteristics of webs of sheet material, such as paper products, as the webs are being manufactured. Examples of characteristics measured using focused radiation beams include color, gloss, brightness, surface moisture, coating and smoothness. When the position of a web of product, referred to as "process" in the industry, deviates from its intended passline or moves relative to a focused beam instrument, measurement errors will typically result. Passline deviation error problems are normally addressed by means of guides which are attached to the instrument to constrain the process while the instrument is scanned over the product.

Unfortunately, in many applications, it is impractical to guide the web or process from the instrument side. In some applications it is not practical to contact the process or product damage occurs. In other applications, the process is measured using instruments located on both of its sides. If each instrument constrains the process, the process is "pinched" between two guides located on its opposite sides.

An example of the process pinching problem is color measurement of paper webs wherein the paper web or process may be backed by a tile of known color. A backing tile is contained in a module on the side of the process opposite to the instrument. For proper calibration of the instrument, the distance between the backing tile and the process must be controlled. However, the process also needs to be maintained at the proper focal distance from the instrument. Thus, the process should be constrained from both sides which would result in pinching the process.

If the process is restrained on only one side, for example on the backing tile side for a paper web color measurement, the color measurement instrument on the opposite side of the process suffers errors resulting from deflection of a scanning frame which typically supports the instrument.

Some instruments transmit a focused radiation beam through a web or product to a reflector located on the opposite side of the web. If the process is restrained on either the transmitter or the reflector side, errors can result when the process moves out of the focal plane of the measuring beam when the scanning frame deflects.

The response of an optical instrument using a focused radiation beam as a function of misalignment or improper focus of the beam on a web of product are typically characterized by a nearly parabolic curve. The instrument or sensor response is maximum when the process is located at the expected passline, i.e. the radiation beam is accurately focused on the process, thus defining the vertex of the parabola. As the instrument or web of product move relative to one another such that the radiation beam is no longer focused on the web, the response of the instrument decreases along the parabolic curve.

If the process is constrained, using a Bernoulli effect hold down device on the reflector or backing tile side of the process, an error in measurement will occur due to deflection between the instrument and the process. If the absolute distance is measured between the instrument and the process or the hold down device, a correction factor can be derived from the instrument response curve, such as the parabolic curve referred to above.

Measurement of absolute distance between the instrument and the process or hold down device for a focused beam measuring device could thus be a solution to the deflection error. Unfortunately, absolute distance measurements having sufficient accuracy, temperature stability and long term stability, which could serve as a compensating measurement are not practical. Devices like optical triangulators, eddy current or magnetic distance sensors can very accurately sense change in distance to the process or hold down device. However, the absolute distance indicated by such instruments may vary with time, temperature or angular alignment.

Accordingly, there is a need for an improved arrangement for compensating for deflection in measuring instruments utilizing a focused radiation beam. Ideally, the arrangement would be inexpensive and simple to implement facilitating its inclusion into new instruments and its retrofitting into many existing instruments.

SUMMARY OF THE INVENTION

This need is met by the method and apparatus of the present invention wherein an instrument utilizing a focused beam of radiation, light in the is used to measure one or more characteristics of a moving sheet or web of material as it is being manufactured. The instrument is positioned on a first side of the web and a reference surface, such as a backing tile in the case of color measurement of a paper web, is placed on the second side of the web. The web of paper is maintained a fixed distance from the reference surface such that variations in the distance of the instrument from the reference surface affect the focus of the beam on the web or process.

In the present invention, the instrument is positioned opposite a reference surface and both are scanned over the web of sheet material by means of a conventional scanning frame. In the illustrated embodiment, the reference surface is one of a plurality of backing tiles carried on a carousel which can be rotated for tile selection. The instrument is moved to an off sheet position for initial and periodic calibration and standardization operations.

In the off sheet position, a first surface comprising one of the backing tiles carried by the carousel is moved into a position opposite to the instrument and at the "nominal" position of the process or web. The instrument measures the first surface. A second surface comprising another one of the backing tiles carried by the carousel is moved opposite to the instrument but spaced farther from or closer to the instrument than the first surface by a defined distance. The instrument then measures the second surface.

The difference between the measurements performed on the first and second surfaces is used to calculate the distance of the instrument from the web of material. The calculated distance of the instrument from the web of material is then used to determine an operating position on an instrument response curve and the instrument is calibrated according to the position on the curve. A second or third order polynomial is fitted to the response curve for the instrument. The selected polynomial is differentiated at the operating point on the curve to determine the rate of change of the measurement characteristic of the instrument at that operating point.

To compensate for deviations or changes in the gap of the instrument or the spacing of the instrument from the process or web of material, gap changes and the determined rate of change of the measurement characteristic are used to compensate the measurements made by the instrument.

In accordance with one aspect of the present invention, a method for operating an instrument utilizing a focused beam to measure at least one characteristic of a sheet of material having first and second sides comprises the steps of: positioning the instrument on a first side of a sheet of material; positioning a reference surface on a second side of the sheet of material, the reference surface being spaced from the instrument to define a gap therebetween for receiving the sheet of material; maintaining a substantially fixed spacing between the sheet of material and the reference surface; determining the distance from the instrument to the sheet of material; calibrating the instrument based on the distance from the instrument to the sheet of material; selecting a rate of change of measurement characteristics of the instrument corresponding to the distance from the instrument to the sheet of material; measuring variations in the gap between the instrument and the reference surface; and, utilizing measured variations in the gap and the selected rate of change of measurement characteristics to compensate for relative deflections between the instrument and the reference surface.

In the illustrated embodiment of the invention, the step of maintaining a substantially fixed spacing between the sheet of material and the reference surface comprises the step of operating a Bernoulli effect hold down device associated with the reference surface. The method may further comprise the step of periodically performing the steps of determining the distance from the instrument to the sheet of material and calibrating the instrument by selecting a rate of change of measurement characteristics of the instrument corresponding to the distance from the instrument to the sheet of material to maintain the instrument in calibration. Currently preferred periods range from approximately one half hour to two hours.

The step of determining the distance from the instrument to the sheet of material may comprise the steps of: taking the instrument off-sheet; measuring a characteristic of a first surface substantially corresponding in position to the sheet of material with the instrument; measuring the characteristic of a second surface spaced a defined distance from the first surface with the instrument; and, utilizing the difference between the measured characteristics of the first and second surfaces to calculate the distance from the instrument to the sheet of material.

The step of calibrating the instrument based on the distance from the instrument to the sheet of material preferably comprises the steps of: fitting a curve to measurement characteristics of the instrument; determining the instrument operating response on the curve based on the determined distance from the instrument to the sheet of material; and, forcing the instrument to read correctly for the curve and the distance.

The step of forcing the instrument to read correctly for the curve and the distance may comprise the steps of: selecting the first surface to have a known measurement on the instrument; and, calibrating the instrument to read correctly when the instrument measures the first surface.

The step of selecting a rate of change of measurement characteristics of the instrument corresponding to the distance from the instrument to the sheet of material preferably comprises the steps of: determining an instrument operating position on the curve based on the determined distance from the instrument to the sheet of material; and, taking the derivative of the curve at the instrument operating position.

In one embodiment of the present invention, the step of determining the distance from the instrument to the sheet of material comprises the steps of: taking the instrument off-sheet; measuring a characteristic of a movable surface placed in a first position substantially corresponding to the sheet of material with the instrument; displacing the movable surface to a second position spaced a defined distance from the first position; measuring the characteristic of the movable surface in the second position with the instrument; and, utilizing the difference between the characteristic of the movable surface measured in the first and second positions to calculate the distance from the instrument to the sheet of material.

In accordance with another aspect of the present invention, a method for operating an instrument utilizing a focused beam to measure at least one characteristic of a sheet of material having first and second sides comprises the steps of: positioning the instrument on a first side of a sheet of material; positioning a reference surface on a second side of the sheet of material, the reference surface being spaced from the instrument to define a gap therebetween for receiving the sheet of material; taking the instrument off-sheet; measuring a characteristic of a first surface substantially corresponding in position to the sheet of material with the instrument; measuring the characteristic of a second surface spaced a defined distance from the first surface with the instrument; utilizing the difference between the measured characteristic of the first and second surfaces to calculate the distance from the instrument to the sheet of material; and, calibrating the instrument based on the calculated distance from the instrument to the sheet of material.

For this aspect of the invention, the method may further comprise the steps of: maintaining a substantially fixed spacing between the sheet of material and the reference surface; selecting a rate of change of measurement characteristics of the instrument corresponding to the distance from the instrument to the sheet of material; measuring variations in the gap between the instrument and the reference surface; and, utilizing measured variations in the gap and the selected rate of change of measurement characteristics to compensate for relative deflections between the instrument and the reference surface.

In accordance with yet another aspect of the present invention, apparatus utilizing a focused beam to measure at least one characteristic of a sheet of material having first and second sides comprises an optical instrument positioned on a first side of a sheet of material for emitting a focused radiation beam toward the first side of the sheet of material, receiving radiation reflected from the first side of the sheet of material to measure a characteristic thereof and generating signals representative of received radiation and thereby the characteristic to be measured. Backing means is positioned on a second side of the sheet of material for selectively placing a reference surface in two positions on the second side of the sheet with the two positions being spaced at two defined distances from the optical instrument. The backing means includes hold down means for maintaining a substantially fixed spacing between itself and the sheet of material. Controller means is provided for receiving signals generated by the optical instrument in response to the reference surface in the two positions and for calibrating the instrument in response thereto.

The apparatus preferably further comprises gap measurement means for measuring variations in distance from the optical instrument to the backing means. In this instance, the controller means further provides for determining the rate of change of measurement characteristics of the instrument at calibration and utilizing the variations in distance from the optical instrument to the backing means to compensate for errors in the signals due to variations in distance from the optical instrument to the backing means.

In the illustrated embodiment, the backing means comprises a carousel for selectively positioning two of a plurality of backing tiles to define the reference surface in the two positions. The backing means further provides for positioning one of the plurality of backing tiles to define a reference surface for operation of the instrument in measuring the at least one characteristic of the sheet. And, the hold down means comprises a Bernoulli effect hold down device.

It is thus an object of the present invention to provide an improved method and apparatus for calibrating an instrument utilizing a focused beam of radiation to measure one or more characteristics of a web of material as the web is being manufactured; to provide an improved method and apparatus for calibrating an instrument utilizing a focused beam of radiation to measure one or more characteristics of a web of material as the web is being manufactured by means of off sheet measurements made by the instrument on two surfaces spaced a defined distance apart from one another, with one of the surfaces being positioned at substantially the same position as the process; and, to provide an improved method and apparatus for calibrating an instrument utilizing a focused beam of radiation to measure characteristics of a web of material as the web is being manufactured wherein an instrument response curve is defined and approximated by a second or third order polynomial which is used for calibration of the instrument and differentiated at an operating point of the instrument for compensation of errors which would otherwise be present due to variations in a process receiving gap of the instrument.

Other objects and advantages of the invention will be apparent from the following description, the accompanying drawings and the appended claims.

BRIEF DESCRIPTION OF THE INVENTION

FIG. 6 is a response curve for an instrument using a focused light beam to make color measurements of a paper web.

DETAILED DESCRIPTION OF THE INVENTION

While the present invention is generally applicable for compensating deflections between an instrument utilizing a focused radiation beam to measure characteristics of webs of material as they are being manufactured, it will be described herein with reference to color measurement of paper webs for which it is initially being applied. It is to be understood that this description in no way limits the scope of the present invention as is set forth in the claims following the description.

Figure 1:
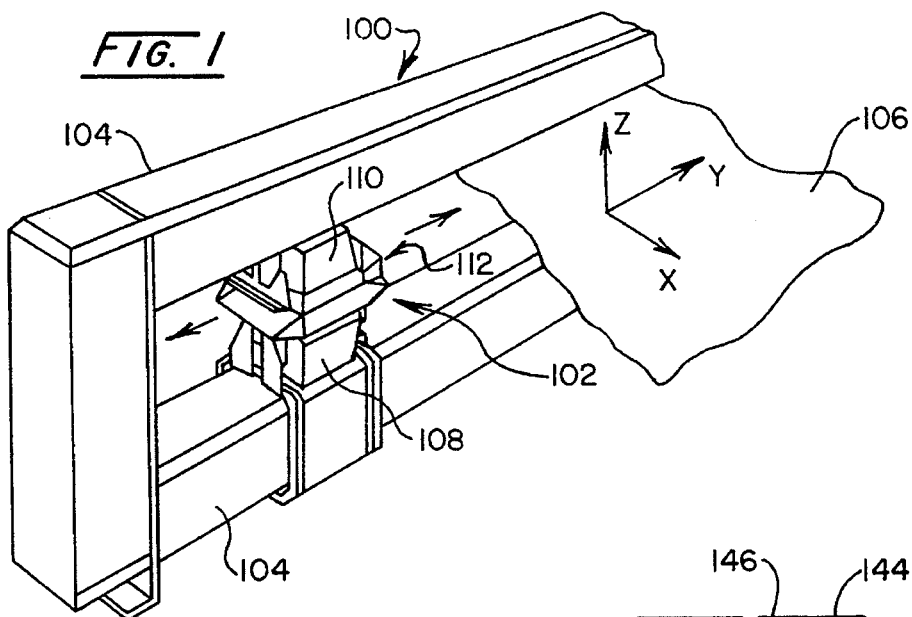
FIG. 1 is a partial perspective view of a scanning system for which the present invention is applicable.

A partially broken-away perspective view of a web scanning system 100 for which the present invention is applicable is shown in FIG. 1. A scanner 102 is moved along a supporting frame which includes two support beams 104 positioned one above a web 106 of material to be scanned and one below the web 106. The scanner 102 includes first and second members or heads 108, 110 which are moved back-and-forth along the beams 104 to scan the web 106 in the cross direction or transversely to its direction of movement during manufacture. The web 106 of material, in this case a paper, is moved in the machine or x direction as indicated by the x axis of a coordinate system shown in FIG. 1 and the cross direction is in the y direction. A gap 112 is formed between the first and second heads 108, 110 with the web 106 of material to be scanned passing through the gap 112 for the scanning operation.

Figure 2:
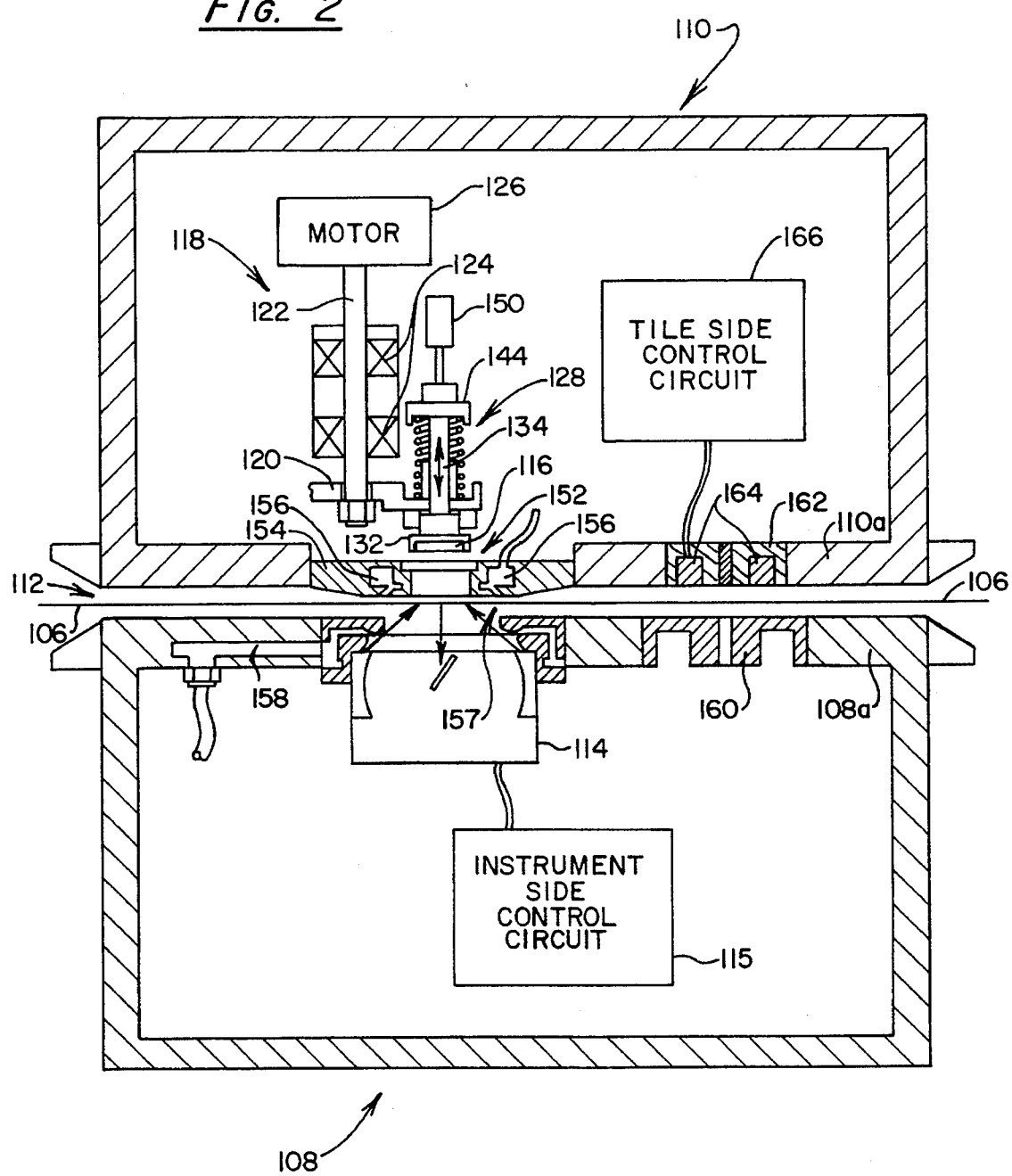
FIG. 2 is a partially sectioned schematic side view of web scanning apparatus of FIG. 1 which can be operated in accordance with the present invention.

As shown in FIG. 2, the first head 108 includes an optical instrument 114 which emits a focused radiation or light beam toward the web 106 and receives light reflected from the web 106 for determining the color of the web 106. The instrument 114 is similar to a Color Checker 545 instrument which is commercially available from Macbeth, a division of Koll Morgen Corp.; however, the instrument has been modified for scanning operation as will be apparent to those skilled in the art.

Figure 3:
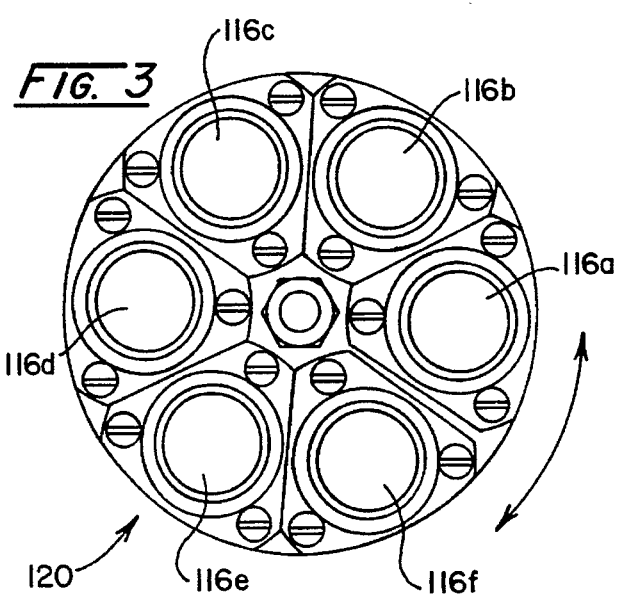
FIG. 3 is a plan view of a rotating tile carousel of the scanning system of FIG. 1.
Figure 5:
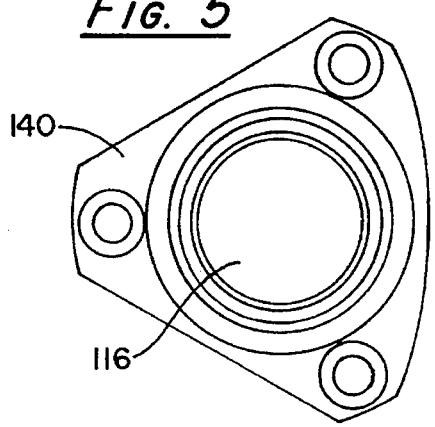
FIG. 5 is a bottom view of the tile holder of FIG. 4.

The instrument 114 generates signals representative of the received light which signals are passed to an instrument side control circuit 115 which processes the signals in accordance with the present invention as will be described hereinafter. For the color measurement which is performed by the instrument 114, the paper web is backed by a tile 116 such that light may also be reflected from the tile 116 to the instrument 114. The tile 116 is supported upon a carousel 118 such that a number of tiles can be positioned opposite to the instrument 114. The carousel 118 includes a tile support ring 120 which is broken away in FIG. 1 and shown in plan view from the bottom of the carousel 118 in FIG. 3. The tile support ring 120 is secured to a shaft 122 which is mounted for rotation within bearings 124 and rotated by a motor 126.

Figure 4:
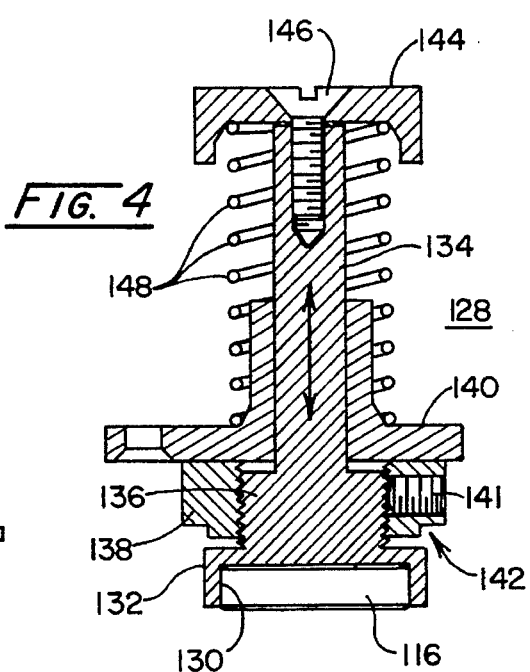
FIG. 4 is a partially sectioned side view of a tile holder of the carousel of FIG. 3.

In the illustrated embodiment, six tiles 116a–116f are mounted within the support ring 120. Each of the tiles 116a–116f are in turn mounted within a tile holder 128, best shown in FIG. 4. As shown in FIG. 4, the tile 116 is mounted within a recess 130 in a lower end or head 132 of a multiple stepped tile support rod 134. The head 132 of the tile support rod 134 is stepped down to a threaded portion 136 which is threadedly engaged with a collar 138. The collar 138 abuts a mounting frame 140 which secures the tile holder 128 to the support ring 120. The collar 138 also receives a set screw 141 for securing the tile support rod 134 at a selected position relative to the collar 138.

The threaded mounting of the tile support rod 134 permits the position of the tile 116 to be precisely positioned relative to a positioning shoulder 142 on the collar 138. A spring retaining cap 144 is secured to the narrow end of the tile support rod 134 by a screw 146. A compression spring 148 is compressed between the cap 144 and the mounting frame 140 to normally retract the tile support rod 134 and collar 138 to the position shown in FIGS. 2 and 4. As shown in FIG. 2, the carousel 118 includes an extender mechanism taking the form of a pneumatic cylinder 150 in the illustrated embodiment. Of course, the extender mechanism can comprise a hydraulic cylinder, solenoid or other actuator as appropriate for a given application.

As shown in FIG. 2, the positioning shoulder 142 seats within a stepped opening 152 within a tile positioning faceplate 154. The faceplate 154 includes an annular plenum 156 with opening channels and holes 157 extending from the plenum 156 to surround the opening 152. When compressed air is applied to the plenum 156, a Bernoulli effect hold down is activated to maintain the web 106 a fixed distance from the faceplate 154. Compressed air is also provided via a plenum 158 adjacent to the instrument 114 to form a cleaning air flow and air bearing across the face of the instrument 114. This air flow substantially prevents web contact with the instrument 114 or head 108 and reduces the possibility of process dirt deposits accumulating thereon.

While the relative positioning of the heads 108, 110 are tightly maintained by the support beams 104 of the supporting frame of FIG. 1, variations, particularly in the z direction or gap 112, do occur. These gap variations or deflections are measured by a gap sensor comprising a ferrite cup 160 mounted into a faceplate 108a of the head 108 and a ferrite cup 162 mounted into the faceplate 110a of the head 110 as shown in FIG. 2.

A winding 164 is secured into cup 162 by epoxy or otherwise and is connected to gap sensing electronics contained within a tile side control circuit 166. The gap sensing electronics preferably comprise an oscillator circuit with the winding 164 forming the inductive element of the oscillator circuit. The frequency of oscillation of the oscillator circuit is related to the inductance defined by the winding 164 which is a function of the gap 112 between the cup 162 and the cup 160. As should be apparent, changes in the gap 112 between the cup 164 and the cup 160 are the same as changes in the gap between the tile 116 and the instrument 114. For additional information regarding the gap measurement apparatus reference is made to U.S. Pat. No. 5,233,195 which is incorporated herein by reference.

The present invention provides for using relative distance measurements made by the gap measurement apparatus described immediately above instead of absolute distance measurements to perform compensation for deflections in the z direction in the system 100 of FIG. 1. The invention thus eliminates problems associated with accurately determining the absolute distance measurement between the instrument 114 and the web 106. In practicing the invention, two of the tiles 116 or samples are used to simulate the process or web 106 in an off-sheet or standardize position. The two tiles 116 have a precisely set vertical distance between them. For example, one tile may be 1 millimeter further from the instrument 114 than the other. Alternately, a single tile can be positioned on an actuating device which causes the tile to move between two positions which are separated by a precisely set distance.

Errors in the readings generated by the instrument 114 due to improper focusing are apparent in the typical, nearly parabolic instrument response curve as shown in the normalized curve 168 of FIG. 6 for the color measurement instrument 114. A response curve may be characterized by a second order polynomial $Y=az^2+bz+c$ or a third order polynomial $Y=az^3+bz^2+cz+d$. The shape of the response curve, fox example the response curve 168 shown in FIG. 6, does not change over time since focus errors are dependent on fixed optical characteristics, such as focal length and the like, which do not change over time.

The distance between the instrument 114 and the process can be calculated by using the instrument 114 to take measurements of tile characteristics at two different distances from the instrument 114. Two tiles at different distances or one tile which is moved between two positions separated from one another can be used, with one of the two tiles or tile positions being substantially at the position of the process while the scanner 102 is positioned to one side thereof or off sheet.

The calculated distance between the instrument 114 and the process is then used to determine the operating position on the response curve 168 of FIG. 6. By taking the differential of the response curve 168 at that point, the rate of change of instrument response for small additional variations in vertical distance at that point is determined. The distance from the instrument 114 to the process, the corresponding point on the response curve 168 and the rate of change for that point on the response curve 168 are determined at periodic instrument calibration-standardization intervals, which should be approximately ever half hour to every two hours depending upon the stability of the instrument 114 and the environmental characteristics of the process being monitored.

When the heads 108, 110 are on-sheet, the gap measurement apparatus described above accurately measures incremental gap changes from the gap which existed when the off sheet measurements were made. Using the rate of change of the instrument response curve which is calculated using the first derivative of the polynomial fitted to the response curve, the change of instrument response versus change in gap is determined. In this way, a correction is determined to correct for errors in the instrument readings due to improper focus based only on measurement of gap deviations or changes from the gap which existed at the time the system 100 was standardized.

When the instrument is initially set up and calibrated, for example at the factory prior to shipment, a set of polynomial coefficients a, b, c or a, b, c, d are determined to fit a response curve corresponding to instrument response Y versus vertical distance z.

In the following description, measurements Y taken by the instrument 114 are described as a fraction of their peak value Yp or in a normalized form Y/Yp. The peak value is the value measured when the process is located exactly at the expected passline, 3.5 mm in FIG. 6. The response characteristics are modeled or curve fitted using the following equation:

$$Y/Yp=az^3+bz^2+cz+d \qquad (a)$$

When the system is periodically standardized, a tile is measured in two vertical positions with a known vertical distance therebetween and hence a known differential distance from the instrument 114. If two tiles having a preset distance from one another are used, they are positioned into the measurement beam from the instrument 114 at two different times. Two tile operation is provided in the illustrated embodiment by two of the tiles 116 with the two tiles being positioned by means of the threads described above and selected by operation of the carousel 118.

In FIG. 6 the response of the instrument is Y/Yp. A first or standardize tile is positioned substantially in the on sheet measurement plane, i.e. it is positioned such that it is substantially in line with the process in the "nominal" process plane, at a position designated Z1, Y1. The nominal process plane corresponds to processes having a thickness of about 10 mils. For processes having different nominal or target thicknesses, the position of the first tile can be changed or, more conveniently, a variable, process, can be added in the equation used to calculate the correct instrument differential response at the process plane. In any event, the reading Y1/Yp corresponds to the measurement taken by the instrument 114 when the standardize or first tile is positioned opposite the instrument 114 and is given by the following equation:

$$Y1/Yp = az^3 + bz^2 + cz + d \tag{1}$$

Next, a reading Y2/Yp is taken with a second or autofocus tile which is displaced a known distance $\delta z$ further from (or closer to) the instrument 114 than the first tile. If equation (1) describes the instrument 114 response for the first tile at Z1 then equation (2) describes the instrument 114 response for the second tile positioned at Z2 and is:

$$Y2/Yp = (a*(z+\delta z)^3 + b*(z+\delta z)^2 + c*(z+\delta z) + d) \tag{2}$$

Deflection, in the illustrated embodiment vertical deflection, causes a multiplicative error in the response Y of the instrument 114. If Y=0, no signal detected, then deflection has no effect. A multiplicative correction factor, cf, can be derived for Y1, during periodic off sheet calibration-standardization, making it agree with its expected peak value, Yp, even if the process is not located at the passline where the peak reading would occur:

$$Yp = Y*cf \text{ and } cf = Yp/Y1$$

Applying the correction factor, cf, to Y1 and Y2:

$$\delta Y = cf*(Y1-Y2) \text{ and};$$

$$\delta Y/Yp = (Y1-Y2)/Y1$$

Accordingly, only the fractional difference between measurements taken by the instrument 114 needs to be calculated, independent of the correction factor cf, in order to exactly describe $\delta Y/Yp$.

From equations (1) and (2) it follows:

$$\delta/Yp = (a*(z+\delta z)^3 + b*(z+\delta z)^2 + c*(z+\delta z) + d) - (Y1/Yp)$$

Solving for z:

$$z = (AB \pm SQRT(B^2 * A*C))/(*A) \tag{3}$$

Where:
A=3*δz*a
B=(3*δz²*a)+(2*δz*b)
C=(δz³*a)=(δz²*b)+(δz*c)+(δY/Yp)

It is noted that only one root will fall in a predetermined range of z corresponding to the distance of the instrument 114 from the web 106. In most instances, it is believed that the positive root is used if the distance between the two tiles used for calibration-standardization in the off sheet position is negative, i.e. the second tile or autofocus tile is closer to the instrument 114 than the first tile or the standardization tile; and, the negative root is used if the distance between the two tiles used for standardization is positive, i.e. the second tile is farther from the instrument 114 than the first tile.

As previously noted, if the thickness of the process is substantially different from a nominal thickness, for example ±2 mils from a nominal 10 mil thickness, then the value of z calculated using equation (3) is modified prior to calibration and calculation of the differential instrument response for the new process thickness. That is the calculated distance of the instrument from the process z is modified by the new target process thickness, z=a+(10−δprocess).

If a second order polynomial, $Y = az^2 + bz + c$, is used to characterize the response of the instrument 114, then:

$$z = A*\delta Y/Yp + B \tag{4}$$

Where:
A=−1/(2*a*δz)
B=(b+a*δz)/(−2*a)

A correction factor, AF, is used to correct subsequent on-line measurements. AF is the derivative of equation (a) and defines the rate of change of Y/Yp at distance z, calculated using Equation (3).

$$AF = (dY/Y)dz \tag{5}$$

$$AF = (*a*z^2) + (2*b*z) + c \tag{6}$$

AF=Correction Factor (AutoFocus)
z=calculated in (3)
a, b, and c are given
dz=δGap, measured on-line with the gap measurement apparatus as described above If a second order curve fit is used to characterize the error due to the instrument 114 being improperly focused on the process, then:

$$AF = (*a*z + b) \tag{7}$$

Two examples of calculating AF for two vertical misalignments will now be described with reference to FIG. 6. In Example 1 the actual gap is 0.500 mm larger than the target gap; and, in Example 2 the actual gap is 0.500 mm smaller than the target gap. In both examples the tile deviation (dTile) or the distance between the standardize tile and the autofocus tile was +0.508 mm. Autofocus or the correction factor, AF, is calculated during the off sheet calibration-standardization routine.

For the two examples: the coefficients a, b, c, d were determined to fit the response curve 168 Y/Yp versus the gap 112; (dTile) is the set or known distance between the two tiles used for calibration-standardization, the standardize tile and the autofocus tile; and, the measurement of % difference in Y values between the two tiles (at standardization) measured by the instrument 114: t,0200

The color measuring optical instrument 114 of FIG. 1 is standardized at vertical distance z, calculated using equation (3). The reflectance values are forced to read correctly when the standardize tile is in position Y1, 3.94 mm in Example 1. If the instrument does not undergo further vertical deflection, the measurements performed by the instrument 114 will be correct. In reality, some vertical deflection is expected. The deviation in the gap 112, relative to the standardized position, is dz in equation (5) and equation (8) given immediately below. The corrected Y value for on-line measurement, Yc, is expressed:

$$Yc = Y * (1 - AF*dz) \tag{8}$$

In practice (1−AF*dz) will be multiplied by percent reflectance for each wavelength from the color measuring optical instrument 114 to facilitate opacity correction algorithms and direct calculation of Z and Y coordinates. Multipliers on reflectance values are equivalent to a multiplier on the Y instrument response value.

To summarize operation of the present invention, the instrument 114 is taken off sheet. A standardize tile, one of the tiles 116, is properly positioned by the carousel 118 and extended by the pneumatic cylinder 150 to a position in alignment with the process being monitored or web 106. A first measurement is then taken with the instrument 114. An autofocus tile, one of the tiles 116, is properly positioned by the carousel 118 and extended by the pneumatic cylinder 150 to a position spaced from the process or web 106, either closer to or farther from the instrument 114 than the web 106. A second measurement is then taken with the instrument 114.

As described above, the distance of the instrument 114 from the process is determined and the instrument 114 is calibrated based on the determined distance and an instrument response curve, for example the response curve 168 as shown in FIG. 6. The system operating point on the response curve has now been established and, by taking the derivative of a polynomial which was fitted to the response curve, the rate of change of the measuring characteristics of the instrument 114 at the operating point is determined.

The instrument 114 is then placed on sheet for measurement of color characteristics of the web 106. The gap measurement apparatus described above is operated to accurately measure incremental gap changes from the gap which existed when the off sheet measurements were made. The incremental gap changes together with the rate of change of the measuring characteristics of the instrument 114 are used to compensate for deviation in the gap 112 and hence changes in the focus of the focused beam on the web 106.

Having thus described the method and apparatus of the present invention in detail and by reference to preferred embodiments thereof, it will be apparent that modifications and variations are possible without departing from the scope of the invention defined in the appended claims.

What is claimed is:

1. A method for operating an instrument utilizing a focused beam to measure at least one characteristic of a sheet of material having first and second sides, said method comprising the steps of:

positioning said instrument on a first side of a sheet of material;

positioning a reference surface on a second side of said sheet of material, said reference surface being spaced from said instrument to define a gap therebetween for receiving said sheet of material;

maintaining a substantially fixed spacing between said sheet of material and said reference surface;

determining the distance from said instrument to said sheet of material;

calibrating said instrument based on the distance from said instrument to said sheet of material;

selecting a rate of change of measurement characteristics of said instrument corresponding to the distance from said instrument to said sheet of material;

measuring variations in said gap between said instrument and said reference surface; and utilizing measured variations in said gap and said selected rate of change of measurement characteristics to compensate for relative deflections between said instrument and said reference surface.

2. A method as claimed in claim 1 wherein said step of maintaining a substantially fixed spacing between said sheet of material and said reference surface comprises the step of operating a Bernoulli effect hold down device associated with said reference surface.

3. A method as claimed in claim 1 further comprising the step of periodically performing said steps of determining the distance from said instrument to said sheet of material and calibrating said instrument by selecting a rate of change of measurement characteristics of said instrument corresponding to the distance from said instrument to said sheet of material to maintain said instrument in calibration.

4. A method as claimed in claim 1 wherein said step of determining the distance from said instrument to said sheet of material comprises the steps of:

taking said instrument off-sheet;

measuring a characteristic of a first surface substantially corresponding in position to said sheet of material with said instrument;

measuring said characteristic of a second surface spaced a defined distance from said first surface with said instrument; and utilizing the difference between the measured characteristics of said first and second surfaces to calculate the distance from said instrument to said sheet of material.

5. A method as claimed in claim 4 wherein the step of calibrating said instrument based on the distance from said instrument to said sheet of material comprises the steps of:

fitting a curve defining measurement characteristics of said instrument versus distance of said instrument from said sheet of material;

determining the instrument operating response on said curve based on the determined distance from said instrument to said sheet of material; and forcing said instrument to read correctly for said curve and said distance.

6. A method as claimed in claim 5 wherein said step of forcing said instrument to read correctly for said curve and said distance comprises the steps of:

selecting said first surface to have a known measurement on said instrument; and calibrating said instrument to read correctly when said instrument measures said first surface.

7. A method as claimed in claim 5 wherein the step of selecting a rate of change of measurement characteristics of said instrument corresponding to the distance from said instrument to said sheet of material comprises the steps of:

determining an instrument operating position on said curve based on the determined distance from said instrument to said sheet of material; and taking the derivative of said curve at said instrument operating position.

8. A method as claimed in claim 1 wherein said step of determining the distance from said instrument to said sheet of material comprises the steps of:

taking said instrument off-sheet;

measuring a characteristic of a movable surface placed in a first position substantially corresponding to said sheet of material with said instrument;

displacing said surface to a second position spaced a defined distance from said first position;

measuring said characteristic of said movable surface placed in said second position with said instrument; and utilizing the difference between the measured characteristics of said movable surface measured in said first and second positions to calculate the distance from said instrument to said sheet of material.

9. A method as claimed in claim 8 wherein the step of calibrating said instrument based on the distance from said instrument to said sheet of material comprises the steps of:

fitting a curve defining measurement characteristics of said instrument versus distance of said instrument from said sheet of material;

determining the instrument operating response on said curve based on said determined distance from said instrument to said sheet of material; and forcing said instrument to read correctly for said curve and said determined distance.

10. A method as claimed in claim 9 wherein said step of forcing said instrument to read correctly for said curve and said determined distance comprises:

selecting said first surface to have a known measurement on said instrument; and calibrating said instrument to read correctly when said instrument measures said first surface.

11. A method as claimed in claim 9 wherein the step of selecting a rate of change of measurement characteristics of said instrument corresponding to the distance from said instrument to said sheet of material comprises the steps of:

determining the instrument operating position on said curve based on the determined distance from said instrument to said sheet of material; and taking the derivative of said curve at said instrument operating position.

12. A method for operating an instrument utilizing a focused beam to measure at least one characteristic of a sheet of material having first and second sides, said method comprising the steps of:

positioning said instrument on a first side of a sheet of material;

positioning a reference surface on a second side of said sheet of material, said reference surface being spaced from said instrument to define a gap therebetween for receiving said sheet of material;

taking said instrument off-sheet;

measuring a characteristic of a first surface substantially corresponding in position to said sheet of material with said instrument;

measuring said characteristic of a second surface spaced a defined distance from said first surface with said instrument;

utilizing the difference between the measured characteristics of said first and second surfaces to calculate the distance from said instrument to said sheet of material; and calibrating said instrument based on said calculated distance from said instrument to said sheet of material.

13. A method as claimed in claim 12 further comprising the steps of:

maintaining a substantially fixed spacing between said sheet of material and said reference surface;

selecting a rate of change of measurement characteristics of said instrument corresponding to the distance from said instrument to said sheet of material;

measuring variations in said gap between said instrument and said reference surface; and utilizing measured variations in said gap and said selected rate of change of measurement characteristics to compensate for relative deflections between said instrument and said reference surface.

14. A method as claimed in claim 13 wherein said step of maintaining a substantially fixed spacing between said sheet of material and said reference surface comprises the step of operating a Bernoulli effect hold down device associated with said reference surface.

15. A method as claimed in claim 12 wherein the step of calibrating said instrument based on the calculated distance from said instrument to said sheet of material comprises the steps of:

fitting a curve defining measurement characteristics of said instrument versus distance of said instrument from said sheet of material;

determining an instrument operating response on said curve based on said calculated distance from said instrument to said sheet of material; and forcing said instrument to read correctly for said curve and said calculated distance.

16. Apparatus utilizing a focused beam to measure at least one characteristic of a sheet of material having first and second sides comprising:

an optical instrument positioned on a first side of a sheet of material for emitting a focused radiation beam toward said first side of said sheet of material, receiving radiation reflected from said first side of said sheet of material to measure a characteristic thereof and generating signals representative of received radiation and thereby said characteristic to be measured;

backing apparatus positioned on a second side of said sheet of material for selectively placing a reference surface in two positions spaced at two defined distances from said optical instrument, said backing apparatus including a hold down device for maintaining a substantially fixed spacing between itself and said sheet of material; and a controller for receiving signals generated by said optical instrument in response to said reference surface in said two positions and for calibrating said instrument in response thereto.

17. Apparatus as claimed in claim 16 further comprising gap measurement apparatus for measuring variations in distance from said optical instrument to said backing apparatus, said controller further providing for determining the rate of change of measurement characteristics of said instrument at calibration and utilizing said variations in distance from said optical instrument to said backing apparatus to compensate for errors in said signals due to variations in distance from said optical instrument to said backing apparatus.

18. Apparatus as claimed in claim 17 wherein said backing apparatus comprises a carousel for selectively positioning two of a plurality of backing tiles to define said reference surface in said two positions.

19. Apparatus as claimed in claim 17 wherein said backing apparatus further provides for positioning one of said plurality of backing tiles to define a reference surface for operation of said instrument in measuring said at least one characteristic of said sheet.

20. Apparatus as claimed in claim 19 wherein said hold down device comprises a Bernoulli effect hold down device.

* * * * *